United States Patent [19]

Nugent

[11] 4,154,229
[45] May 15, 1979

[54] BLOOD COLLECTION SYSTEM WITH VENIPUNCTURE INDICATOR

[75] Inventor: Edward L. Nugent, North Caldwell, N.J.

[73] Assignee: Becton, Dickinson and Company, East Rutherford, N.J.

[21] Appl. No.: 823,416

[22] Filed: Aug. 10, 1977

[51] Int. Cl.$^2$ ............................................. A61B 5/00
[52] U.S. Cl. .................................................. 128/764
[58] Field of Search ................. 128/2 F, DIG. 5, 272, 128/276, 215

[56] References Cited

U.S. PATENT DOCUMENTS

| 3,734,080 | 5/1973 | Petterson et al. | 128/DIG. 5 |
| 3,877,465 | 4/1975 | Miyake | 128/2 F |
| 3,886,930 | 6/1975 | Ryan | 128/2 F |
| 4,079,729 | 3/1978 | Cornell | 128/2 F |

FOREIGN PATENT DOCUMENTS 469055  2/1952  Italy .................................. 128/DIG. 5

Primary Examiner—John D. Yasko
Attorney, Agent, or Firm—Kane, Dalsimer, Kane, Sullivan & Kurucz

[57] ABSTRACT

A blood sample collection system including an indicator for denoting successful venipuncture prior to entry into an evacuated tube portion of the system. The system includes a double ended cannula open at both ends and having a passageway therethrough. A holder is provided for mounting the cannula thereon with one end extending forwardly and adapted for venipuncture and the other end extending rearwardly and being adapted for coupling with a sample collection container. The evacuated sample collection container has a closed end and an open end with the open end closed by a self-sealing puncturable stopper. The stopper is adapted to be penetrated by the rear end of the cannula to provide fluid communication between the passageway through the cannula and the interior of the sample collection container. A pressure responsive indicator is on the stoppered collection container and is adapted to physically deform when the one end of the cannula is introduced into the vein and the other end of the cannula is introduced a predetermined distance into the stopper. The deformation is sufficient to permit a small amount of blood to enter the cannula for visual observation of a successful venipuncture. Indexing structure is on the holder and stoppered container to facilitate relative positioning of the stopper and cannula end penetrating therethrough in at least one position to facilitate venipuncture and operation of the pressure responsive indicator.

11 Claims, 8 Drawing Figures

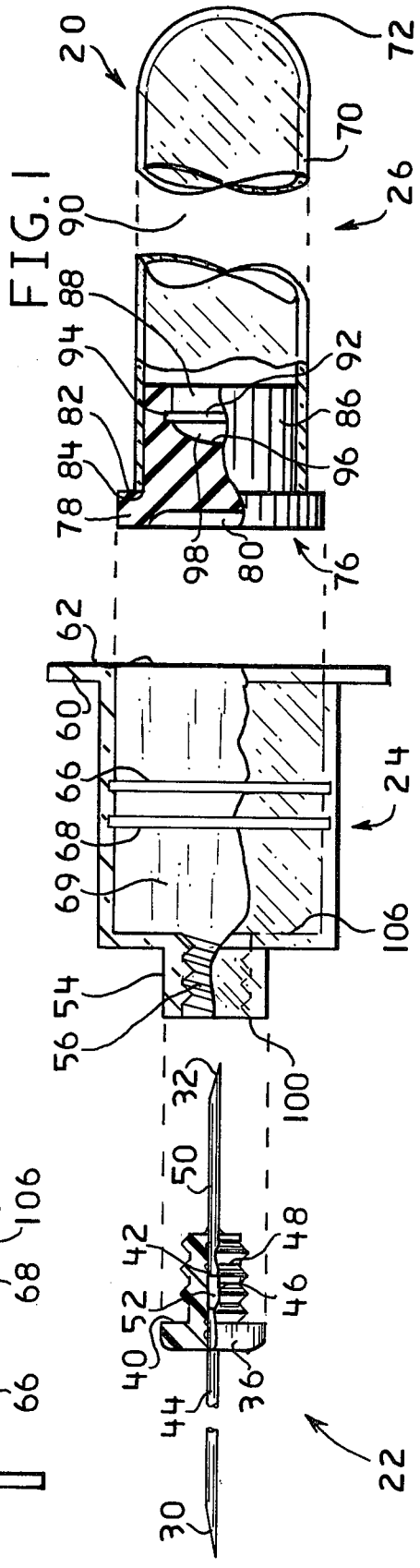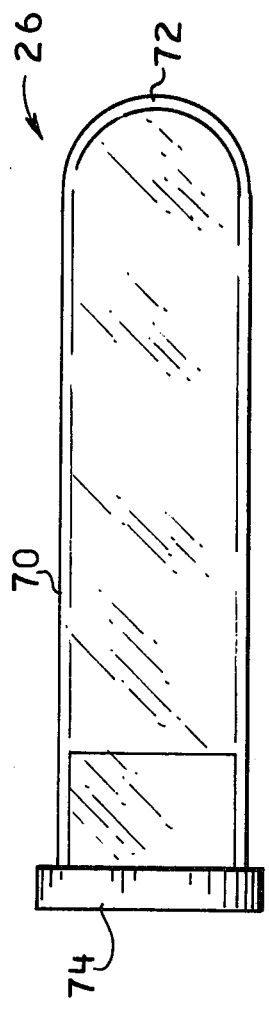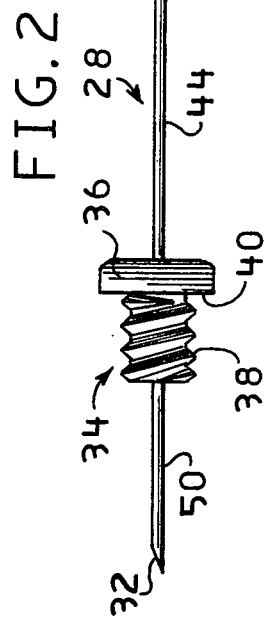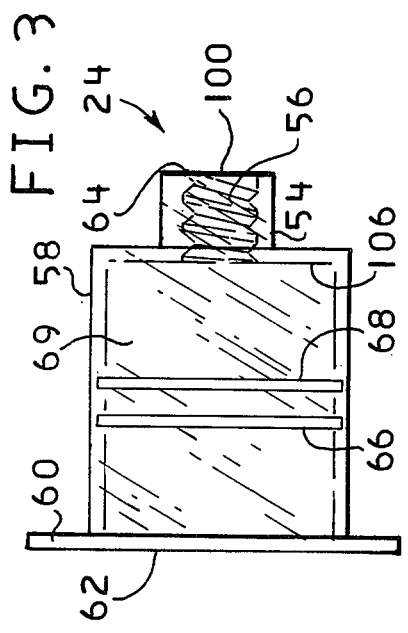

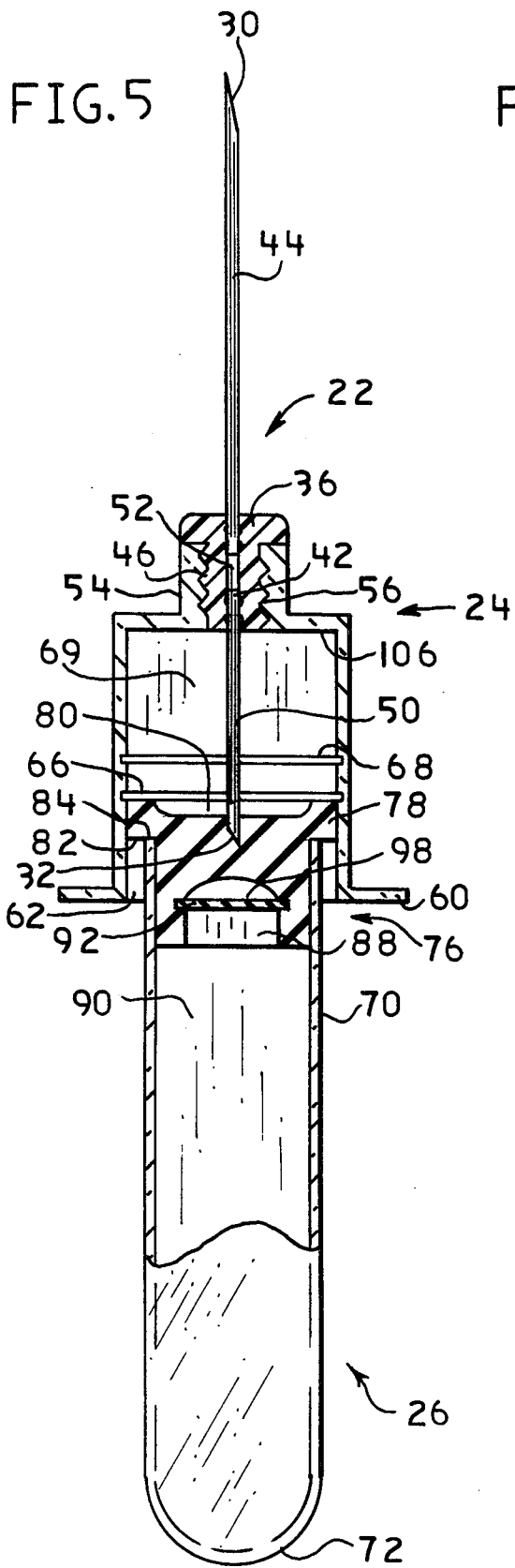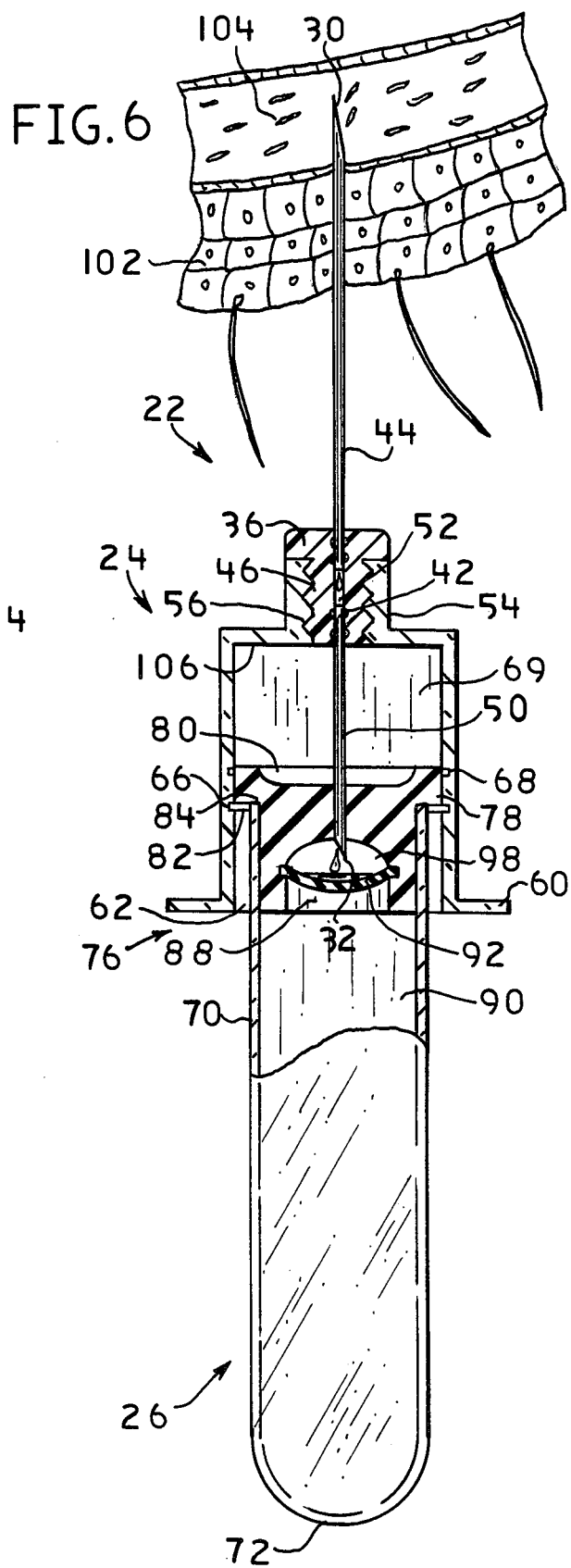

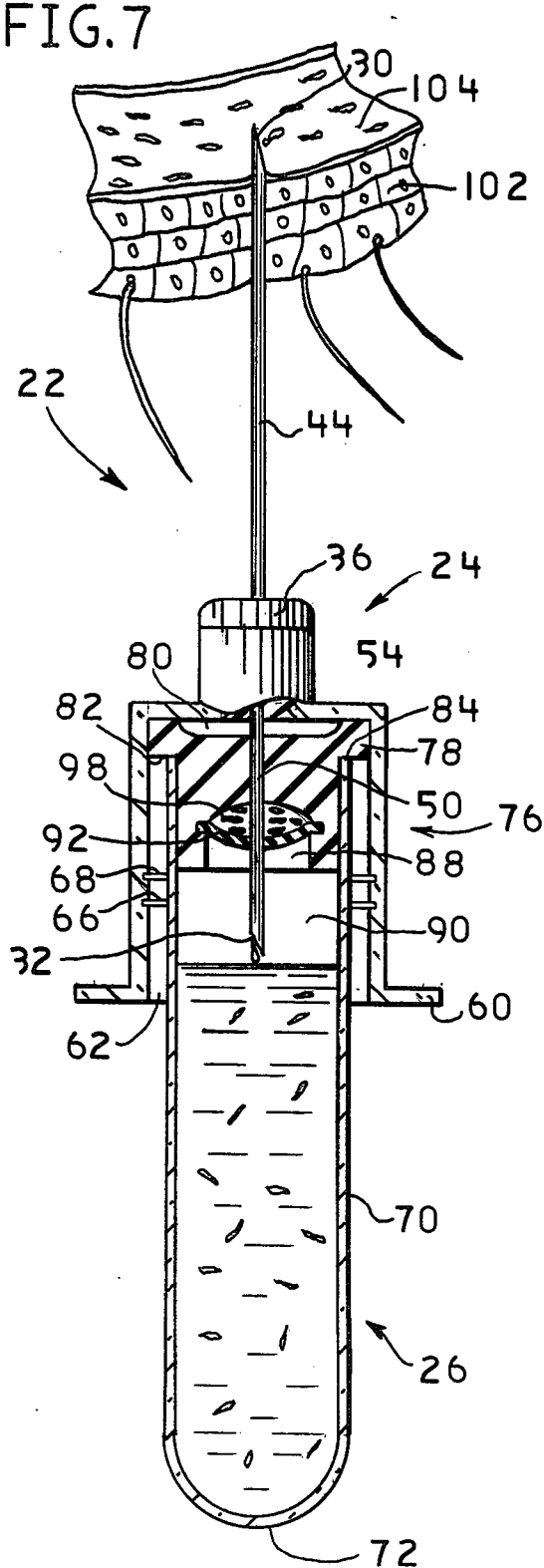
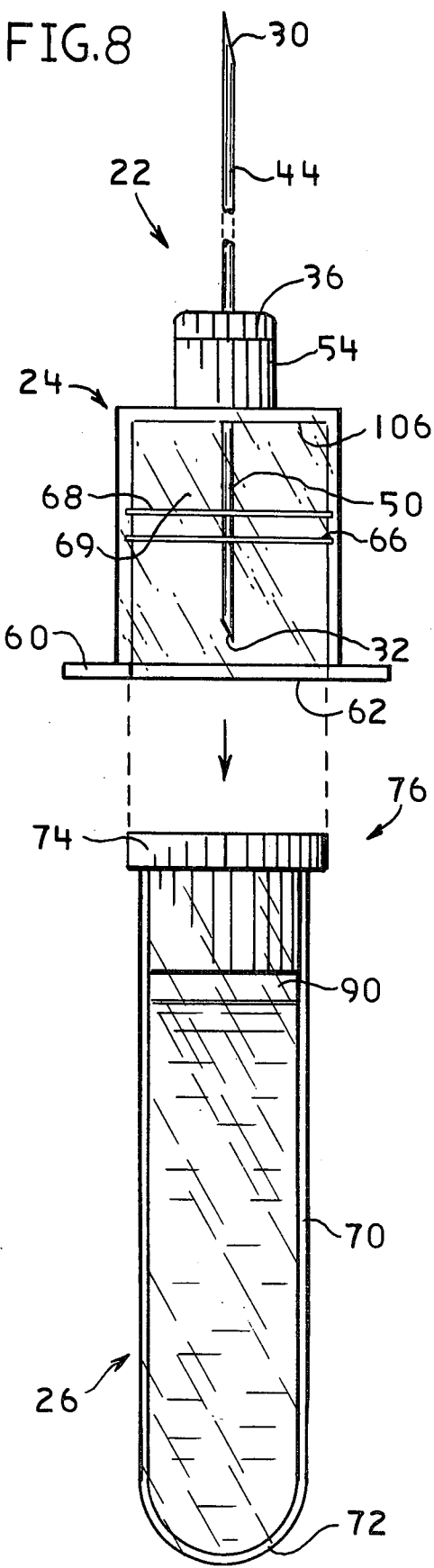

BLOOD COLLECTION SYSTEM WITH VENIPUNCTURE INDICATOR

BACKGROUND OF THE INVENTION

Vacuum blood collection systems are well known in the art and have been utilized for a number of years. The basic patent for this type of system is U.S. Pat. No. 2,460,641. The conventional system employs a double ended needle with a hub intermediate its ends which is adapted to be mounted to a holder so that one end of the needle extends forwardly of the holder and the rear end of the needle extends into an interior hollow chamber in the holder. The rear end of the holder is open to permit introduction of a stoppered evacuated tube into alignment with the rear end of the needle so that the needle can penetrate the stopper and communicate with the interior of the container. When the forward end of the cannula is introduced into a vein and the rear end of the cannula is introduced into an evacuated tube, the pressure differential between the venous pressure and the evacuated tube will cause blood to flow into the tube for collection of a blood sample. U.S. Pat. Nos. 3,965,889; 3,890,955 and 3,817,240 are examples of this conventional system.

Throughout the years various improvements have been made to the collection system such as by providing various types of valves to shut-off flow from the vein while evacuated tubes are interchanged for purposes of collecting a multiplicity of samples. Examples of this type of arrangement are present in U.S. Pat. Nos. 3,494,352 and 3,469,572.

Further improvements in the basic system have employed various types of blood tell tales to indicate correct positioning of the device in the vein. Examples of this type of structure are depicted in U.S. Pat. Nos. 3,942,514; 3,886,930 and 3,817,240.

Another improvement in the basic structure includes the provision of indexing means on the holder and stoppered tube for purposes of indicating the relative position of the stopper and the cannula. U.S. Pat. No. 3,366,103 is representative of this stage of development in the art.

The number of blood samples being collected for testing and analysis is ever increasing and the need for more improved sampling systems of a simple and disposable nature for mass use is ever present.

SUMMARY OF THE INVENTION

With the above background in mind, it is among the primary objectives of the present invention to provide a system which utilizes the accepted and conventional method of collecting blood specimens, that is a double ended needle, a holder for the needle, and an evacuated stoppered tube and, additionally, provides structure permitting the visual indication of successful venipuncture without requiring entry into the evacuated tube by the blood collection needle.

A further objective is to provide a conventional holder of transparent or translucent material with guide lines on the holder to indicate positioning of the evacuated tube in the holder to index a position of the end of the needle within the stopper for venipuncture and for indicating purposes to denote a successful venipuncture when the stoppered tube is coupled with one end of the needle.

It is also contemplated that the double ended needle can be formed of two separate needle portions mounted in a hub having a passageway therethrough so that one needle portion extends from one end of the hub and the other needle portion extends from the other end of the hub. The hub is formed of a transparent plastic or other suitable material to permit observation of the portion of the passageway through the hub between the ends of the cannula portions so that when blood is permitted to enter the base between the needle portions it will be visible thereby indicating a successful venipuncture.

A further objective is to provide a flexible diaphragm or membrane mounted on the rubber stopper and positioned to provide a small chamber between the undersurface of the stopper and the diaphragm. When the stopper and diaphragm are positioned within the evacuated tube and venous pressure is transmitted to one part of the diaphragm, due to communication of the double ended cannula with the chamber between the diaphragm and the bottom of the stopper, the pressure differential will permit expansion of the diaphragm thereby increasing the volume in the passageway and permitting blood to flow a predetermined distance through the cannula until it is at a point where it is visibly observable through the assembly thereby indicating a successful venipuncture.

A further objective is to position the diaphragm on the stopper so that full insertion of the stoppered tube within the holder will permit one end of the double ended cannula to pass through the stopper and diaphragm and provide fluid communication between the vein and the evacuated tube.

The dimensions of the assembly and the materials utilized are chosen from a conventional range of sizes and material so as to permit only enough blood to fill the space between the ends of the two cannula halves within the hub where it is visually observable to indicate a successful venipuncture.

Naturally it is contemplated that other pressure responsive means can be provided to deform and increase the volume within the system when subjected to a differential between venous pressure and the pressure within the evacuated container. Also, in place of the spaced cannula portions within the hub to provide the intermediate chamber which is visibly observable, other indicating passageways are possible in order to bring the predetermined amount of blood to a desired location for visual observance.

Also, the indexing means in the holder can be repositioned as long as it serves to index the position on the stopper with respect to the holder and consequently with respect to the cannula mounted in the holder so that a positive positioning of the stopper with respect to the cannula can be easily and effectively attained for first, fixing a penetration position of the end of the cannula in the stopper for venipuncture, and second, positioning of the end of the cannula within the stopper to activate the indicator means so that a predetermined amount of blood will enter the assembly to a point for visual observance of a successful venipuncture.

The system including the indexing means and indicating means is inexpensive and easy and efficient to utilize thereby maintaining a low cost design for the device which is adaptable to mass production.

In summary, a blood collection system is provided which includes a double ended cannula open at both ends and having a passageway therethrough. A holder is provided having means thereon for mounting the cannula with one end extending forwardly and adapted for venipuncture and the other end extending rearwardly and adapted for coupling with a sample collection container. An evacuated sample collection container is provided having a closed end and an open end with the open end being closed by a self-sealing puncturable stopper adapted to be penetrated by the rear end of the cannula to provide fluid communication between the passageway through the cannula and the interior of the sample collection container. A pressure responsive indicator means is on the stoppered collection container and is adapted to physically deform when the one end of the cannula is introduced into the vein and the other end of the cannula is introduced a predetermined distance into the stopper. The deformation is sufficient to permit a small amount of blood to enter the cannula for visual observation of the successful venipuncture. Indexing means is on the holder and stoppered container to facilitate positioning of the stopper in a first position with the cannula having penetrated the predetermined distance for the one end to be introduced into the vein with the other end being closed by the stopper and to facilitate positioning of the stopper in a second position with the cannula having penetrated to a degree to permit operation of the pressure responsive means and a small amount of blood to flow into the cannula for visual observation.

With the above objectives among others in mind, reference is made to the attached drawings.

BRIEF DESCRIPTION OF THE DRAWINGS

FIG. 1 is an exploded partially sectional elevation view of the system of the invention;

FIG. 2 is a side elevation view of the needle assembly portion of the invention;

FIG. 3 is a side elevation view of the holder portion of the invention;

FIG. 4 is a side elevation view of the stoppered container portion of the invention;

FIG. 5 is a sectional elevation view of the system of the invention showing the components in coupled relative position for venipuncture;

FIG. 6 is a sectional elevation view thereof showing the components of the system in relative coupled position after a successful venipuncture and the pressure responsive indicator portion indicating a successful venipuncture;

FIG. 7 is a sectional elevation view thereof showing the components of the system in relative position for collection of the sample from the vein into the collection tube; and FIG. 8 is an elevation view of the system after the needle has been removed from the vein and the stoppered tube containing the collected sample has been uncoupled from the needle assembly and holder.

DETAILED DESCRIPTION

All of the components of blood collection system 20 is depicted in FIG. 1 and the three separate component assemblies are depicted in FIGS. 2-4. Needle assembly 22 is depicted in FIG. 2, holder 24 is depicted in FIG. 3 and container assembly 26 is depicted in FIG. 4.

The depicted embodiment of the invention is of the type commonly used for collection of a blood sample from the vein of a patient. While the present invention is particularly useful in that environment, it is also contemplated that the pressure responsive indicating means and indexing structure is equally useful in other environments where samples are being transferred from one vessel to the other and where pressure differential conditions between the vessels exist.

Needle assembly 22 includes a double ended cannula 28 having a pointed forward end 30 used for venipuncture and a pointed rear end 32 used for puncture through the stopper of an evacuated collection tube. Intermediate the ends of the double ended cannula is a hub 34. The hub's outer surface includes a flanged end portion 36 and a threaded body portion 38 of lesser diameter than the flanged end portion. The undersurface 40 of the flanged end 36 forms a resting surface with a portion of the holder as will be discussed in detail below. As depicted in FIG. 1, the hub 34 has a passageway 42 therethrough. The cannula 28 is formed of a first hollow needle portion 44 which extends from flange 36 of the hub and terminates in pointed end 30 utilized for venipuncture. The rear tip 46 of hollow needle portion 44 terminates within passageway 42 in hub 34. Spaced from the end 46 of hollow needle portion 44 is the end 48 of a second hollow needle portion 50 which extends from hub 34 and terminates in pointed end 32 used for puncture of the stopper in the collection tube. The two hollow needle portions together form the double ended cannula 28. They have their ends affixed within passageway 42 of hub 34 in a conventional manner, such as by epoxy. The space between ends 46 and 48 of the hollow needle portions 44 and 50 respectively forms a blood indicating chamber 52. This chamber is visible through the hub structure by making the hub 34 transparent or translucent.

Holder 24 as depicted in FIG. 3 includes a forward tubular boss 54 having a threaded passageway 56 therethrough. The threaded passageway has a diameter which corresponds to the diameter of the threaded outer surface 38 of hub 34 whereby relative rotation therebetween will couple the needle assembly 22 to holder 24.

Extending from the rear end of tubular boss 54 is an enlarged diameter having a hollow tubular body 58. Tubular body 58 terminates at its rear end in an annular rim 60. An opening 62 is positioned in the rear end of body 58 and an opening 64 is in the forward end of the body in communication with the threaded passageway 56 through boss 54.

Intermediate the ends of the hollow interior chamber 69 in body 58 are a pair of annular lines 66 and 68 which are parallel to one another and spaced from one another to form two indexing lines on holder 24. The lines are formed in a conventional manner, such as by molding colored media in the body walls or painting or otherwise marking the interior or exterior wall of the body 58. The body is formed of a translucent or transparent material such as plastic which is designed so that the index lines 68 and 66 are readily visible through the walls of body 58. Similarly, hub 34 of needle assembly 22 is formed of a conventional transparent plastic or other well known substitute therefor. Cannula 28 is formed of a conventional needle material such as a low cost steel which can be easily sharpened for penetration purposes and which can be easily lubricated such as by use of a silicone to facilitate penetration by its ends.

The container assembly 26 as depicted in FIGS. 1 and 4 includes a conventional collection tube or container 70 having a closed end 72 and an open end 74. The tube or container 70 is formed of a conventional low cost disposable material such as glass and is also usually conveniently transparent for visual observation of collection of a sample therein. The open end 74 of tube 70 is closed and sealed by a self-sealing puncturable stopper 76. Conventionally, the stopper is formed of a resilient rubber material, either natural or synthetic, which will seal the end of the tube and which will permit its penetration to introduce fluids to the interior of container 70. In operation, tube 70 is evacuated and maintained in that evacuated condition by the seal formed by stopper 76 in the open end 74 of the tube.

The stopper has an enlarged head 78 with an exposed upper surface 80 and an annular flanged undersurface 82 which seats on the upper open rim 84 of the tube. Extending from the undersurface of head 78 is a narrower diameter body 86 which is introduced into the end portion of the tube and sealingly engages with the inner side wall of the tube. A recess 88 is formed in the undersurface of the stopper in communication with the evacuated interior 90 of tube 70. Mounted along the length of recess 88 is a diaphragm 92 of a highly flexible nonporous material such as rubber. Diaphragm 92 is mounted in conventional fashion to the stopper such as by seating the edge thereof in an accommodating annular recess 94. It can be fixed in place by frictional interengagement or by other conventional means such as epoxy or appropriate adhesives. The diaphragm 92 is spaced from the end wall 96 of recess 88 to form a sealed cavity or chamber 98 therebetween.

In operation, needle assembly 22 is coupled with hub 24 by screwing threaded portion 38 into the threaded opening 56 of boss 54 with hollow needle portion 44 extending into the interior of body portion 58. The needle assembly is fully threaded until undersurfaces 40 of flange 36 engages with the forward rim 100 of boss 54. Container assembly 26 is then inserted into the body 58 of holder 24 through open end 62 of the holder and onto the cannula 22 by permitting the pointed end 32 of the cannula to penetrate stopper 76 through end wall 80. Penetration is continued until the leading edge of end wall 80 is even with the first guide line 66 in holder 24. The components are then in assembled condition for use. All components of system 20 are predimensioned so that in this condition, point 32 rests within the main body portion of stopper 76 and is closed by the stopper. The tip 32 has not been introduced a sufficient distance to communicate with cavity or chamber 98 at the base of the stopper. This condition prevents vacuum loss through the cannula and is illustrated in FIG. 5.

Thereafter, the system in the condition shown in FIG. 5 is maneuvered and positioned so that end 30 of the cannula is introduced into the vein of a patient. A successful introduction of the cannula 22 into the vein of a patient is depicted in FIG. 6 where the tip 30 has passed through tissue 102 and entered vein 104 containing blood. Once it is believed that venipuncture has been successfully achieved, container assembly 26 is pushed forward within holder 24 until the leading edge of end wall 80 is even with the second guide line 68 in body 58 of the holder. The system is dimensioned so that in this position, the rear pointed end 32 of cannula 22 will have entered cavity 98 and is located in the cavity between the base wall 96 of recess 88 and the adjacent surface of diaphragm 92. In this position, the differential in pressure between the venous pressure in vein 104 and the low pressure or vacuum in tube 70 causes the flexible diaphragm 92 to deflect or stretch away from base wall 96 of the recess and toward the closed end 72 of tube 70. This in turn increases the volume of cavity 98 causing blood to be displaced from the vein 104 through hollow needle portion 44 of cannula 22 and into transparent hub 34. Materials and dimensions are chosen so that substantially only enough blood to fill hollow needle portion 44 and the cavity 52 in the hub between end 46 of hollow needle portion 44 and spaced end 48 of hollow needle portion 50 is accumulated. Naturally it is not necessary that this amount of blood be controlled in a very precise or accurate manner as long as the amount permitted to enter is within a range to maintain the blood within the cannula 22. It is a relatively small amount of blood that is permitted to flow for indicating purposes.

The blood in cavity or space 52 is visible through the coupled transparent boss 54 of holder 24 and hub 34 of needle assembly 22. This condition is depicted in FIG. 6.

Thereafter, as depicted in FIG. 7, container assembly 26 can be pushed all the way into holder 24 until the leading edge of end surface 80 of the stopper engages the bottom wall 106 of body 58. This permits point 32 to fully penetrate stopper 76 completing fluid communication between the vein 104 and the interior 90 of tube 70. The pressure differential between the partially or fully evacuated tube 70 and the venous pressure of vein 104 will cause blood to flow from the vein into the tube for collection of the appropriate blood sample.

Blood will collect within container 70 until pressure is equalized between the vein and the interior of the tube whereupon the blood flow will stop. This is generally readily visually observable through the walls of tube 70. Thereafter, as depicted in FIG. 8 pointed end 30 of cannula 22 can be removed from vein 104 and container assembly 26 can be withdrawn from holder 24 whereupon pointed end 32 of the cannula will withdraw through self-sealing stopper 76. The self-sealing stopper will once again seal the end of the container assembly 26 leaving an uncoupled stoppered container assembly for further handling and testing procedures.

It should be kept in mind that if stopper 76 is moved to the second guide line 68 as depicted in FIG. 6, and successful venipuncture has not been achieved, the various subcutaneous layers of tissue 102 will prevent any apparent pressure differential between the pointed open end 30 of cannula 22 and cavity 98 in container assembly 26. Thus, the pressure differential across diaphragm 92 will be zero and any deflection of the diaphragm 92 will be prevented. This effect will yield no visible blood in the needle hub 34 as would occur with a successful venipuncture as described above. At that time, with an unsuccessful venipuncture, the container assembly 26 is partially withdrawn from holder 24 until the leading edge of end wall 80 of stopper 76 is once again even with the first guide line 66. In this condition which is the arrangement depicted in FIG. 5, the entire assembly 20 can be withdrawn from the patient including removal of cannula end 30 without loss of vacuum in tube 70. Thereafter, another attempt can be made to achieve successful venipuncture by repeating the above mentioned procedure.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A blood collection system comprising:

A double ended cannula open at both ends and having a passageway therethrough;

a holder having means thereon for mounting the cannula with one end extending forwardly and adapted for venipuncture and the other end extending rearwardly and adapted for coupling with a sample collection container;

an evacuated sample collection container having a closed end and an open end with the open end being closed by a self-sealing puncturable stopper adapted to be penetrated by the rear end of the cannula to provide fluid communication between the passageway through the cannula and the interior of the sample collection container;

pressure responsive indicator means on the stoppered collection container adapted to physically deform when the one end of the cannula is introduced into the vein and the other end of the cannula is introduced a predetermined distance into the stopper, the deformation being sufficient to permit a small amount of blood to enter the cannula for visual observation of the successful venipuncture; and indexing means on the holder and stoppered container to facilitate relative positioning of the stopper and cannula end penetrating therethrough in at least one position to facilitate venipuncture and operation of the pressure responsive indicator means.

2. The invention in accordance with claim 1 wherein the indexing means includes positioning means to facilitate positioning of the stopper in a first position with the cannula having penetrated the stopper a predetermined distance for the other end to be closed by the stopper and the one end to be introduced into the vein and to facilitate positioning of the stopper in a second position with the cannula having penetrated the stopper a second predetermined distance to permit operation of the pressure responsive means to let the small amount of blood to flow from the vein into the cannula for visual observation.

3. The invention in accordance with claim 1 wherein the pressure responsive indicator means includes a flexible diaphragm mounted on the stopper in position to be deformed by a pressure differential created by introduction of the forward end of the needle into the vein and passage of the rear end of the needle a predetermined distance into the stopper to communicate with the diaphragm, the diaphragm expanding under the force of venous pressure in contrast to the vacuum in the container thus producing an increase in volume and permitting blood to flow from the vein into the cannula.

4. The invention in accordance with claim 3 wherein the stopper has a recess in its undersurface positioned within the evacuated tube, the diaphragm mounted intermediate the ends of the recess to form a sealed cavity between the surface of the diaphragm and the undersurface of the stopper, the undersurface of the stopper forming the base of the recess so that penetration of the rear end of the cannula through the stopper into the sealed cavity in the recess will permit pressure through the cannula to deform the diaphragm toward the evacuated tube interior exposed to the other side of the diaphragm and permitting blood to flow from the vein into the cannula a predetermined distance for observation, the diaphragm adapted to be penetrated by the rear end of the cannula when the stopper is shifted along the cannula thereby providing communication between the interior of the cannula and the interior of the evacuated tube for collection of a sample of blood.

5. The invention in accordance with claim 4 wherein the stopper has an enlarged head portion and a narrow diameter body portion extending from one side of the head portion, the undersurface of the head portion adjacent to the body portion resting on the rim surrounding the open end of the evacuated collection container and the outer surface of the body portion engaging with the adjacent side wall of the upper end portion of the evacuated tube to seal the open end of the tube, the recess in the stopper being in the end thereof distal from the head end and in direct communication with the evacuated interior of the container, the diaphragm being mounted intermediate the ends of the recess with the one side in communication with the evacuated interior of the tube and the other side in communication with the sealed cavity in the recess in the stopper.

6. The invention in accordance with claim 1 wherein the cannula is formed of two separate hollow needle portions mounted on a hub, the first needle portion extending from one side of the hub and having the one end of the cannula thereon and the other needle portion extending rearwardly of the hub and forming the other end of the cannula, the first and second needle portions being mounted in a passageway through the hub and having their ends mounted therein spaced from one another, the space in the passageway through the hub located between the inner ends of the two needle portions forming a visual chamber for observation of blood introduced through the cannula upon a successful venipuncture.

7. The invention in accordance with claim 1 wherein the holder includes a tubular boss extending from a wider diameter hollow tubular body, the boss and body having a passageway therethrough and the hollow interior of the body being of sufficient diameter to slidably receive the container therein, one end of the cannula extending from the free end of the boss and the other end of the cannula extending from the other end of the boss interiorally of the body in position for coupling with the container.

8. The invention in accordance with claim 7 wherein the indexing means includes an annular line on the surface of the tubular body, the line being observable and forming a first index point with the stopper of the collection container to locate a first position for the cannula within the stopper to facilitate venipuncture.

9. The invention in accordance with claim 8 wherein a second line is formed on the body spaced from the first line and closer to the end of the holder containing the boss, the second line cooperating with the top of the stoppered collection container inserted into the cage portion of the holder so that when the stopper is aligned with the second line, the stopper will be in a second position and the cannula will be in position in the stopper for operation of the pressure sensitive tube indicating means.

10. The invention in accordance with claim 7 wherein the boss has a central passageway therethrough with a threaded surface thereon, the cannula being mounted in a hub positioned intermediate its ends, the hub having a threaded outer surface for threaded interengagement with the threaded inner surface of the boss to facilitate coupling of the cannula to the holder.

11. The invention in accordance with claim 5 wherein an annular groove is positioned intermediate the ends of the side walls of the recess, the diaphragm being positioned with its annular edge fixed in position in the annular groove.

* * * * *